United States Patent [19]

Miller

[11] 4,409,408
[45] Oct. 11, 1983

[54] INHIBITING POLYMERIZATION OF VINYL AROMATIC MONOMERS

[75] Inventor: Richard F. Miller, Humble, Tex.

[73] Assignee: Atlantic Richfield Company, Los Angeles, Calif.

[21] Appl. No.: 423,409

[22] Filed: Sep. 24, 1982

[51] Int. Cl.³ .................................................. C07C 7/18
[52] U.S. Cl. .......................................... 585/4; 585/3; 585/5; 585/950
[58] Field of Search ....................... 585/2, 3, 4, 5, 428, 585/950

[56] References Cited

U.S. PATENT DOCUMENTS

| 2,809,155 | 10/1957 | Buehler | 585/4 |
| 2,867,672 | 1/1959 | Hemmerich | 585/4 |
| 3,248,440 | 4/1966 | Albert | 585/4 |
| 3,287,430 | 11/1966 | Haines et al. | 585/4 |
| 3,390,198 | 6/1968 | Leston | 585/3 |

FOREIGN PATENT DOCUMENTS

| 763313 | 9/1980 | U.S.S.R. | 585/5 |
| 819078 | 4/1981 | U.S.S.R. | 585/5 |

Primary Examiner—Delbert E. Gantz
Assistant Examiner—A. Pal
Attorney, Agent, or Firm—C. R. Reap; D. M. Kozak; J. C. Martin, Jr.

[57] ABSTRACT

Vinyl aromatic compounds are stabilized against undesired polymerization by adding to the vinyl aromatic compounds small amounts of N,N-dialkylhydroxylamine and tertiary alkylcatechols. The synergistic effect of the mixture has been demonstrated.

9 Claims, No Drawings

INHIBITING POLYMERIZATION OF VINYL AROMATIC MONOMERS

FIELD OF THE INVENTION

The present invention relates to the stabilization of ethylenically unsaturated compounds and more particularly to the inhibition of undesired polymerization of vinyl aromatic compounds during storage, shipping or processing.

BACKGROUND

Vinyl aromatic compounds such as styrene undergo undesired spontaneous polymerization (i.e. polymerization of monomers due to heat or the random generation of free radicals in the monomers) during storage, shipping or processing. The problem is particularly acute during purification operations carried out at elevated temperatures such as distillation. Spontaneous polymerization is disadvantageous not only because it causes fouling of distillation column reboilers and other equipment used for processing the vinyl aromatic monomer but also because it usually renders the monomer unfit for use without further treatment. Accordingly, it is desirable and often necessary to inhibit the spontaneous polymerization of vinyl aromatic monomers.

PRIOR ART

To prevent spontaneous polymerization of vinyl aromatic monomers it is common practice to add to the monomers compounds which have polymerization inhibiting activity. A wide variety of such compounds, known as polymerization inhibitors, have been used for this purpose. Sulfur has been widely used in the past to inhibit polymerization of vinyl aromatic compounds, however sulfur usage is undesirable because large quantities of sulfur are required for effective polymerization inhibition. This presents a waste removal problem when the monomer is separated from the sulfur-monomer mixture, which is accomplished by distillation. The distillation bottoms product, which contains higher molecular weight hydrocarbons, polymer and sulfur, cannot be burned due to the air pollution hazard caused by sulfur oxides. Thus, this material must be disposed of by burial in a waste dump.

In recent times, many chemical compounds have been developed as substitutes for sulfur in polymerization inhibiting applications. These compounds have been used as polymerization inhibitors for vinyl aromatic monomers with varying degrees of success. U.S. Pat. No. 3,390,198, issued to Leston, discloses the use of several mono and dialkylcatechols as polymerization inhibitors for hot styrene. U.S. Pat. Nos. 4,061,545 and 4,177,110 issued to Watson, discloses the use of a combination of tertiary-butylcatechol and phenothiazine as a polymerization inhibitor system for vinyl aromatic compounds. U.S. Pat. No. 3,148,225, issued to Albert, employs dialkylhydroxylamines for inhibiting popcorn polymers formation in styrene-butadiene rubbers. The dialkylhydroxylamine compounds appear to react with and terminate free radicals which cause undesired formation of polymers. U.S. Pat. Nos. 2,965,685, issued to Campbell, discloses inhibiting polymerization by adding about 5 ppm to 5 percent dialkylyhydroxyamine to styrene monomer. Sato et al., in U.S. Pat. No. 3,849,498, teach the use of diethylhydroxylamine as a polymerization inhibitor for an alcoholic solution of unsaturated aldehydes. MayerMader et al., U.S. Pat. No. 3,878,181, employ diethylhydroxylamine either alone or in combination with a water soluble amine such as triethanolamine to terminate the aqueous emulsion polymerization of chloroprene.

It has now been discovered that mixtures of N,N-dialkylhydroxylamines and tertiary alkyl pyrocatechols, commonly referred to as tertiary alkylcatechols, provide outstanding polymerization inhibiting activity for vinyl aromatic monomers. Thus, because of the synergistic effect of these mixtures it is now possible to provide unexpectedly superior polymerization inhibiting protection with the same total equivalent weight of N,N-dialkylhydroxylamines and tertiary alkylcatechol mixtures than is obtainable by the use of members of either of these groups of compounds by themselves.

Accordingly, it is object of the invention to present stable compositions of vinyl aromatic monomers. It is another object of the invention to present a method of effectively and economically inhibiting spontaneous polymerization of styrene and other vinyl aromatic monomers. These and other objects of the invention are set forth in the following description and examples of the invention.

SUMMARY OF THE INVENTION

According to the invention the protection of vinyl aromatic monomers against spontaneous polymerization is accomplished by incorporating into the monomers mixtures of one or more dialkylhydroxylamines, each alkyl group of which has 2 to 10 carbon atoms, and one or more tertiary alkylcatechols, the tertiary alkyl group of which has 4 to 20 carbon atoms.

DETAILED DESCRIPTION OF THE INVENTION

The term vinyl aromatic monomer as used in this description includes any of the readily polymerizable vinyl aromatic compounds, e.g. styrene, alpha alkyl styrene, such as alpha methyl styrene, ring alkyl substituted styrene such as p-methyl styrene, diethylenically substituted benzene compounds, such as divinylbenzene, etc. and mixtures thereof.

The N,N-dialkylhydroxylamine compounds used in the invention have the structural formula

RR'NOH wherein R and R' are the same or different straight or branched-chain alkyl groups having 2 to about 10, and preferably 2 to 6, carbon atoms. Although N,N-dialkylhydroxylamines having more than about 10 carbon atoms in each alkyl group may be useful in the invention it is peferred that compounds containing 10 or fewer carbon atoms in each alkyl group be used in the invention because the latter compounds are commercially available. Mixtures of two or more N,N-dialkylhydroxylamines can also be advantageously used in the compositions of the invention.

Suitable N,N-alkylhydroxylamines include N,N-diethydroxylamine, N,N-dibutylhydroxylamine, N,N-butylethylhydroxylamine, N,N-didecylhydroxylamine, N,N-2-ethylbutyloctylhydroxylamine, etc. Examples of preferred N,N-dialklyhydroxylamines include N,N-diethylhydroxylamine and N,N-dibutylhydroxylamine. As noted above, two or more of these compounds may be used in combination, if desired.

Tertiary alkylcatechol compounds useful in the invention are those having the structural formula

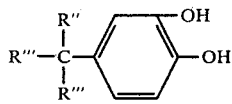

wherein R'', R''' and R'''' are the same or different alkyl groups and the total number of carbon atoms in R'' R''' and R'''' may vary from 3 to 20 or more. The total number of carbon atoms in R'', R''' and R'''' may exceed 20 but no particular advantage is derived from the use of such high molecular weight compounds. The alkyl groups may be straight or branched-chain. Preferred tertiary alkylcatechols are those in which the total number of carbon atoms in R'', R''' and R'''' in the above formula is 3 to 10. Mixtures of two or more tertiary alkylcatechols may be used in the invention is desired.

Suitable tertiary-alkylcatechols include p-(t-butyl) catechol, p-(1,1-dimethylethyl)catechol, p-(1-ethyl-1-methyl hexyl)catechol, p-(1,1-diethylpropyl)catechol, p-tributylmethylcatechol, p-trihexylmethylcatechol, etc. Preferred tertiary-alkylcatechols include p-(t-butyl)catechol, p-(1,1-diethylethyl)catechol, etc.

Some N,N-dialkylhydroxylamines, such as N,N-diethylhydroxylamine, and tertiary-alkylcatechols, such as p-tertiary-butyl catechol, are available commercially. Those N,N-dialkylhydroxylamines and tertiary-alkylcatechols which are not commercially available may be prepared by any of the well known techniques. The preparation of these compounds forms no part of the present invention.

The relative concentrations of N,N-dialkylhydroxylamine and tertiary alkylcatechol used in the invention are generally in the range of about 10 to 90 weight percent N,N-dialkylhydroxylamine and 90 to 10 weight percent tertiary-alkylcatechol, based on the total combined weight of these components. In perferred embodiments the concentrations generally fall in the range of about 25 to 75 weight percent N,N-dialkylhydroxylamine and 75–25% tertiary alkylcatechol, based on the total combined weight of these components.

The polymerization inhibiting compositions of the invention are well suited for protecting the reboiler sections of a distillation column during distillation of vinyl aromatic monomers because of the high boiling point of these inhibitor compounds. They may be used at temperatures up to about 150° C. or higher at atmospheric pressure. Since the boiling point of various members of each of the two classes of compounds, i.e. dialkylhydroxylamines and tertiary alkylcatechols, are different, compounds which have the desired boiling point can be easily selected from each class. To make up for the inhibitor which is left behind during distillation, additional inhibitor can be added to the vinyl aromatic monomer after it is distilled from heavier hydrocarbons. In some cases it may be desirable to use lower boiling polymerization inhibitors in combination with the inhibitor compositions of the invention. For example, when distilling a vinyl aromatic monomer from higher boiling hydrocarbons it may be advantageous to add a polymerization inhibitor which has a boiling point near or lower than the boiling point of the vinyl aromatic compound. This will provide protection to the overhead portion of the column. It may also be desirable to add with the polymerization inhibitor compositions of the invention other agents, such as corrosion inhibitors, to provide additional protection to process equipment.

The polymerization inhibitor compositions of the invention can be introduced into the monomer to be protected by any conventional method. It is generally introduced just upstream of the point of desired application by any suitable means, such as by the use of a proportionating pump. The polymerization inhibitor composition may be added as a concentrate but it is preferable to add it as a solution which is compatible with the monomer being treated. Suitable solvents include kerosene, naphtha, the lower alkanes such as hexane, aromatic solvents, such as toluene, alcohols, polyols or ketone, etc. It is often preferable to dissolve the inhibitors of the invention in the monomer to which the inhibitor is being added to avoid introducing additional impurities to the monomer. The concentration of polymerization inhibitor in the solvent is desirably in the range of about 1 to 30 weight percent and preferably about 5 to 20 weight percent based on the total weight of inhibitor and solvent.

The polymerization inhibitor is used at a concentration which is effective to provide the desired protection against spontaneous polymerization. It has been determined that amounts of polymerization inhibitor in the range of about 0.5 to 1000 ppm based on the weight of the monomer being treated affords ample protection against undesired polymerization. For most applications the inhibitor is used in amounts in the range of about 5 to 500 ppm.

The polymerization inhibiting composition can be easily removed from the vinyl aromatic monomer prior to polymerization by caustic washing. Such procedures are well known and commonly practiced to separate phenolic type inhibitors, such as tertiary butylcatechol, from monomers.

The following examples will serve to further illustrate the invention. Unless otherwise stated, parts and percentages are on a weight basis. In the examples styrene, which is representative of vinyl aromatic monomers, was used as the test monomer. In the tests sodium ion, in the form of sodium hydroxide, and benzoyl peroxide were added to the test samples to provide a more intensive test of the ability of the inhibitor compositions of the invention to inhibit spontaneous polymerization. Sodium ions and benzoyl peroxide are both known addition polymerization catalysts for vinyl aromatic monomers.

EXAMPLE I (Control)

To distilled styrene was added sufficient sodium hydroxide (as a 50% aqueous solution) to produce a mixture containing 17 mg of sodium hydroxide per each 1000 grams of styrene monomer. This concentration of sodium hydroxide in the monomer is equivalent to a sodium ion concentration of 10 ppm. One hundred grams of the styrene monomer mixture was introduced into a 250 ml Erlenmeyer flask fitted with a ground glass stopper. Two hundred ppm, based on the weight of styrene, of benzoyl peroxide was added to the flask and the flask was then purged of air by bubbling nitrogen gas through the monomer. After the nitrogen purge the ground glass stopper was inserted into the flask and the flask was placed in an oven. The temperature of the oven was raised to and maintained at a temperature of 90°±2° C. for the duration of the test. Ten ml samples were drawn from the flask every 30 minutes over a two hour period. The samples were carefully drawn under a nitrogen blanket to ensure that no atmospheric air entered the flask.

Each sample was tested to determine the amount of styrene polymer formed by the following procedure: The 10 ml sample of styrene monomer was introduced into 100 ml of cold methanol, quenching the polymerization reaction. The methanol-monomer mixture was heated sufficiently to coagulate the polymer formed. The polymer was recovered from the methanol by filtration, dried overnight at a temperature of 100° F. and weighed. The percentage of polymer formed was determined and reported in the Table in the Run 1 row.

EXAMPLE II (Comparative)

The procedure and tests of Example I were repeated except that 500 ppm of 4,6-dinitro-o-cresol was added to the Erlenmeyer flask just prior to the initial nitrogen purge. The styrene monomer was periodically tested as indicated in Example I. The results are tabulated in the Table in the Run 2 row.

EXAMPLE III (Comparative)

The procedure and tests of Example II were repeated except that 150 ppm of tertiary-butylcatechol was substitured for the 4,6-dinitro-o-cresol. The results are tabulated in the Table in the Run 3 row.

EXAMPLE IV (Comparative)

The procedure and tests of Example II were repeated except that 150 ml of di-n-butyl hydroxylamine was substituted for the 4,6-dinitro-o-cresol. The results are tabulated in the Table in the Run 4 row.

EXAMPLE V

The procedure and tests of Example II were repeated except that the 4,6-dinitro-o-cresol was replaced by a mixture of 75 ppm tertiary butylcatechol and 75 ppm of di-n-butyl hydroxylamine. The results are tabulated in the Table in the Run 5 row.

EXAMPLE VI

The procedure and tests of Example V were repeated except that the 75 ppm of di-n-butyl hydroxylamine was replaced by 75 ppm of diethyl hydroxylamine. The results are tabulated in the Table in the Run 6 row.

TABLE

| Run | Inhibitor | Inhibitor Concentration, ppm | Time Min. 30 | 60 | 90 | 120 |
|---|---|---|---|---|---|---|
| | | | Weight % Polymer Formed | | | |
| 1 | None | — | 0.12 | 1.28 | 3.20 | 8.06 |
| 2 | 4,6-dinitro-o-cresol | 150 | 0.43 | 1.34 | 2.90 | 3.7 |
| 3 | t-butylcatechol | 150 | 0 | 0 | 0.108 | 1.19 |
| 4 | di-n-butyl hydroxylamine | 150 | 0 | 0 | 0.17 | 0.88 |
| 5 | t-butylacatechol di-n-butyl hydroxylamine | 75 75 | 0 | 0 | 0 | 0.41 |
| 6 | t-butylcatechol diethylhydroxylamine | 75 75 | 0 | 0 | 0 | 0.30 |

The benefit of the use of the polymerization inhibitor compositions of the invention are shown in the Table. In the Table the uninhibited monomer contained 8.06 percent polymer after two hours; the Run 2 monomer sample, which was inhibited by a widely used styrene polymerization inhibitor, 4,6-dinitro-o-cresol, contained 3.7% polymer at the end of the two hour period; the two hour analysis of the Run 3 and Run 4 samples, which each contained one of the components of the inhibitor system of the invention, showed polymer concentrations of 1.19% and 0.88% respectively; the two hour analysis of the Run 5 sample which contained the inhibitor composition of the invention showed a polymer concentration of 0.41%. Thus, the inhibitor system of the invention used at 150 ppm shows a greater than two-fold improvement over the use of the next most effective inhibitor, di-n-butylhydroxylamine, at the same concentration. Run 6 shows a modification of the invention in which a different dialkyl hydroxylamine was used. The result obtained is significantly better than that shown in the comparative examples.

Although the invention is described with particular reference to specific examples, it is understood that the invention includes obvious variants. For example, dialkyl hydroxylamines other than di-n-butyl hydroxylamine can be used in the invention and the inhibitor system can be formulated to contain more than one member from each of the two specified classes of compounds. The scope of the invention is limited only by the breadth of the appended claims.

What is claimed is:

1. A composition comprised of (a) a vinyl aromatic compound containing an amount effective to inhibit polymerization of said vinyl aromatic compound of a mixture of (1) about 10 to 90 parts by weight of at least one N,N-dialkylhydroxylamine wherein the alkyl groups are the same or different and each alkyl group has 2 to 10 carbon atoms, and (2) about 90 to 10 parts by weight of at least one tertiary-alkylcatechol having 4 to 20 carbon atoms.

2. The composition of claim 1 wherein the total concentration of said mixture of N,N-dialkylhydroxylamine and tertiary-alkylcatechol in said composition is 0.5 to 1000 ppm, based on the total weight of vinyl aromatic compound.

3. The composition of claim 1 wherein the vinyl aromatic compound is styrene or alkyl substituted styrene, each alkyl group in (1) has 2 to 6 carbon atoms, the tertiary alkyl group in (2) has 4 to 8 carbon atoms and the relative concentrations of the compounds in (1) and (2) are 25 to 75 parts by weight and 75 to 25 parts by weight respectively and the total concentration of said mixture of N,N-dialkylhydroxylamine and tertiary-alkylcatechol is said composition is 5 to 500 ppm, based on the total weight of vinyl aromatic compound.

4. The composition of claim 3 wherein the vinyl aromatic compound is styrene, the compound in (1) is N,N-diethylhydroxylamine and the compound in (2) is tertiary butylcatechol.

5. In a method of inhibiting polymerization of a vinyl aromatic compound comprising adding to the vinyl aromatic compound an amount of an polymerization inhibiting agent effective to substantially reduce the rate of polymerization, the improvement comprising using as the agent a combination of:

(a) about 10 to 90 parts of at least one N,N-dialkylhydroxylamine wherein the alkyl groups are the same or different and each alkyl group has 2 to 10 carbon atoms, and (b) about 90 to 10 parts of at least one tertiary alkyl-catechol having 4 to 20 alkyl carbon atoms per 100 total parts by weight of the compounds in 8a) and (b).

6. The improved method of claim 5 wherein said agent is added to the vinyl aromatic compound in a concentration of about 0.5 to 1000 ppm based on the weight of said vinyl aromatic compound.

7. The improved method of claim 5 wherein each alkyl group of the compound in (a) has 2 to 6 carbon atoms, the tertiary alkyl group of the compound in (b) has 4 to 8 carbon atoms and said agent is added to the vinyl aromatic monomer in a concentration of about 5 to 500 ppm, based on the weight of said vinyl aromatic compound.

8. The improved method of claim 7 wherein the compound in (a) is N,N-diethythyhydroxylamine and the compound in (b) is tertiary-butylcatechol.

9. The improved method of claim 5, 6, 7 or 8 wherein the compounds in (a) and (b) are present in amounts of about 25 to 75 parts and 75 to 25 parts by weight, respectively.

* * * * *